United States Patent
Grill et al.

(10) Patent No.: US 10,576,271 B2
(45) Date of Patent: Mar. 3, 2020

(54) SYSTEMS AND METHODS FOR UTILIZING MODEL-BASED OPTIMIZATION OF SPINAL CORD STIMULATION PARAMETERS

(71) Applicant: Duke University, Durham, NC (US)

(72) Inventors: Warren M. Grill, Durham, NC (US); Bryan Howell, Durham, NC (US); Shivanand P. Lad, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 15/845,127

(22) Filed: Dec. 18, 2017

(65) Prior Publication Data

US 2018/0104479 A1 Apr. 19, 2018

Related U.S. Application Data

(63) Continuation of application No. PCT/US2016/037571, filed on Jun. 15, 2016.
(Continued)

(51) Int. Cl.
*A61N 1/05* (2006.01)
*A61N 1/36* (2006.01)
(Continued)

(52) U.S. Cl.
CPC .............. *A61N 1/0551* (2013.01); *A61N 1/05* (2013.01); *A61N 1/36* (2013.01); *A61N 1/36071* (2013.01);
(Continued)

(58) Field of Classification Search
None
See application file for complete search history.

(56) References Cited

U.S. PATENT DOCUMENTS 6,788,790 B1 9/2004 Leysieffer
7,146,223 B1 12/2006 King
(Continued)

FOREIGN PATENT DOCUMENTS

CA 2837225 A1 12/2012

OTHER PUBLICATIONS

ISA/KR, International Search Report and Written Opinion for PCT Patent Application No. PCT/US2016/037571, dated Oct. 12, 2016.
(Continued)

*Primary Examiner* — Ankit D Tejani
(74) *Attorney, Agent, or Firm* — NK Patent Law

(57) ABSTRACT

Systems, methods, and devices are disclosed for optimizing patient-specific stimulation parameters for spinal cord stimulation. A patient-specific anatomical model is developed based on a pre-operative image, and a patient-specific electrical model is developed based on the anatomical model. The inputs to the electric model are chosen, and the model is used to calculate a distribution of electrical potentials within the modeled domain. Models of neural elements are stimulated with the electric potentials and used to determine which elements are directly activated by the stimulus. Information about the models inputs and which neural elements are active is applied to a cost function. Based on the value of the cost function, the inputs to the optimization process may be adjusted. Inputs to the optimization process include lead/electrode array geometry, lead configuration, lead positions, and lead signal characteristics, such as pulse width, amplitude, frequency and polarity.

19 Claims, 9 Drawing Sheets

Related U.S. Application Data

Figure 1A:
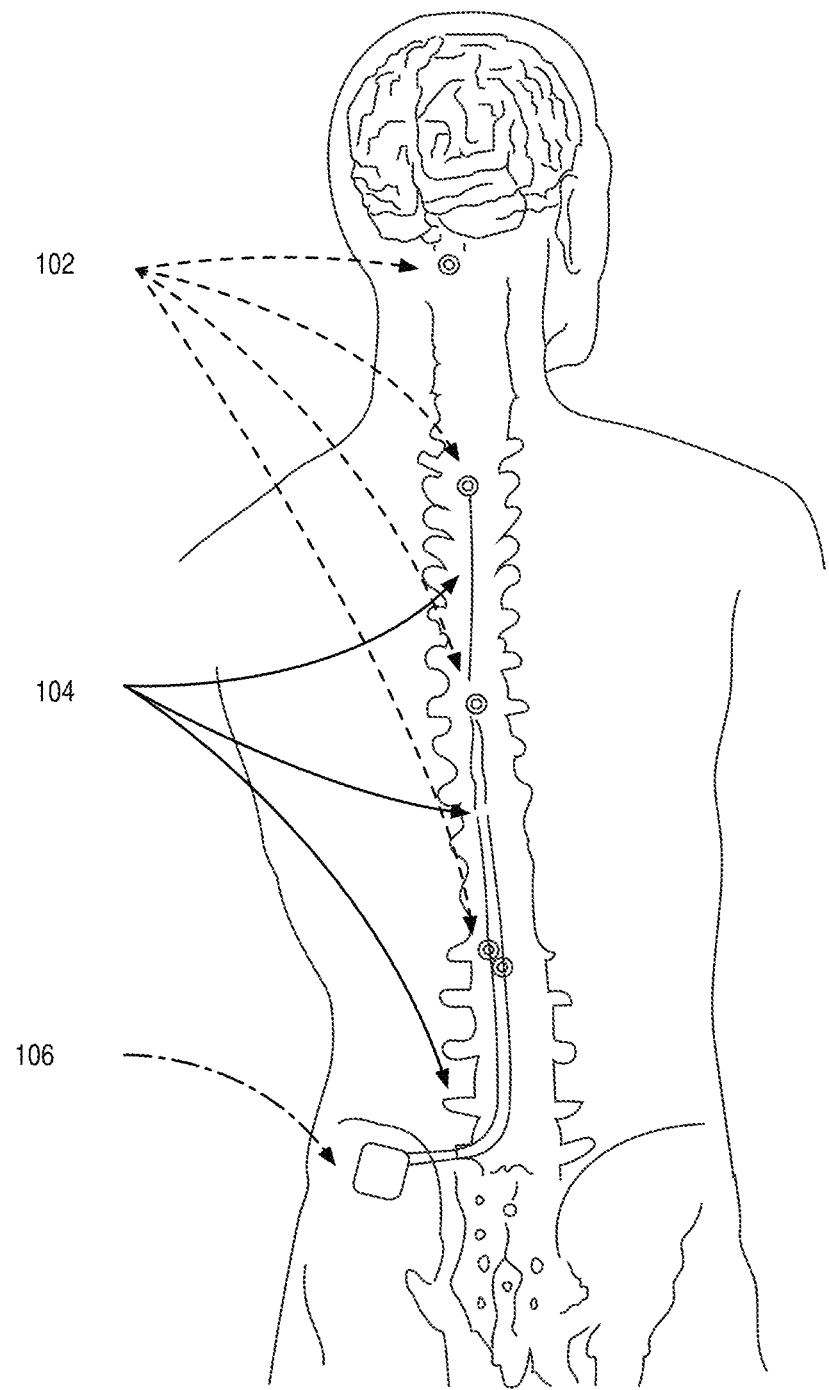

(60) Provisional application No. 62/183,216, filed on Jun. 23, 2015.

(51) Int. Cl.
*G16H 20/30* (2018.01)
*G16H 50/50* (2018.01)

(52) U.S. Cl.
CPC ......... *A61N 1/36128* (2013.01); *G16H 20/30* (2018.01); *G16H 50/50* (2018.01); *A61N 1/36125* (2013.01)

(56) References Cited

U.S. PATENT DOCUMENTS

| | | | |
|---|---|---|---|
| 7,881,805 | B2 | 2/2011 | Bradley |
| 7,991,482 | B2 | 8/2011 | Bradley |
| 2010/0280570 | A1 | 11/2010 | Sturm et al. |
| 2011/0066407 | A1* | 3/2011 | Butson ............ A61B 5/0538 703/2 |
| 2012/0310140 | A1 | 12/2012 | Kramer et al. |
| 2013/0231715 | A1 | 9/2013 | Grill, Jr. et al. |
| 2014/0094872 | A1 | 4/2014 | Fisher et al. |
| 2014/0371515 | A1* | 12/2014 | John ............ A61N 1/3605 600/13 |
| 2014/0379043 | A1 | 12/2014 | Howard |
| 2015/0134031 | A1* | 5/2015 | Moffitt ............ A61N 1/37264 607/62 |

OTHER PUBLICATIONS

WIPO, International Preliminary Report on Patentability for PCT Patent Application No. PCT/US2016/037571, dated Dec. 26, 2017.
Howell, B., et al., "Evaluation of Intradural Stimulation Efficiency and Selectivity in a Computational Model of Spinal Cord Stimulation", PloS one, Dec. 23, 2014, p. e114938, vol. 9.
Bossetti, Chad A., et al., "Analysis of the Quasi-Static Approximation for Calculating Potentials Generated by Neural Stimulation", Journal of Neural Engineering, Mar. 2008, pp. 44-53, vol. 5.
Butson, Christopher R., et al., "Patient-Specific Analysis of the Volume of Tissue Activated During Deep Brain Stimulation", Neuroimage, Jan. 15, 2007, pp. 661-670, vol. 34.
Chaturvedi, Ashutosh, et al., "Patient-Specific Models of Deep Brain Stimulation: Influence of Field Model Complexity on Neural Activation Predictions", Brain Stimulation, Apr. 2010, pp. 65-77, vol. 3.
Elliott, H. Chandler, "Cross-Sectional Diameters and Areas of the Human Spinal Cord", The Anatomical Record, Department of Anatomy, Medical College of the State of South Carolina, 1945, pp. 287-293, vol. 93.
Feirabend, H.K.P., et al., "Morphometry of Human Superficial Dorsal and Dorsolateral Column Fibres: Siginifincance to Spinal Cord Stimulation", Brain, May 1, 2002, pp. 1137-1149, vol. 125.
Glad, Issachar, et al., "Sagittal evaluation of elemental geometrical dimensions of human vertebrae", Journal of Anatomy, 1985, pp. 115-120, vol. 143.
Hernández-Labrado, Gabriel R., et al., "Spinal cord direct current stimulation: finite element analysis of the electric field and current density", Medical & Biological Engineering & Computing, Apr. 1, 2011, pp. 417-429, vol. 49.
Holsheimer, Jan, "Which Neuronal Elements are Activated Directly by Spinal Cord Stimulation", Neuromodulation, Jan. 2002, pp. 25-31, vol. 5, No. 1.
Holsheimer, Jan, et al., "Effects of electrode geometry and combination on nerve fibre selectivity in spinal cord stimulation", Medical & Biological Engineering & Computing, Sep. 1, 1995, pp. 676-682, vol. 33.
Holsheimer, Jan, et al., "Optimum electrode geometry for spinal cord stimulation: The narrow bipole and tripole", Medical & Biological Engineering & Computing, Sep. 1, 1997, pp. 493-497, vol. 35.
Manola, Ljubomir, et al., "Technical Performance of Percutaneous and Laminectomy Leads Analyzed by Modeling", Neuromodulation: Technology at the Neural Interface, 2004, pp. 231-241, vol. 7, No. 4.
McIntyre, Cameron C., et al., "Modeling the Excitability of Mammalian Nerve Fibers: Influence of Afterpotentials on the Recovery Cycle", Journal of Neurophysiology, 2002, pp. 995-1006, vol. 87.
Ohnishi, Aiko, et al., "Morphometry of Myelinated Fibers of Fasciculus Gracilis of Man", Journal of the Neurological Sciences, 1976, pp. 163-172, vol. 27.
Ranck, Jr., James B., et al., "The Specific Impedance of the Dorsal Columns of Cat: An Anisotropic Medium", Experimental Neurology, 1965, pp. 451-463, vol. 11.
Rosenow, Joshua M., et al., "Failure modes of spinal cord stimulation hardware", Journal of Neurosurgery: Spine, 2006, pp. 183-190, vol. 5.
Sankarasubramanian, V., et al., "Electrode alignment of transverse tripoles using a percutaneous triple-lead approach in spinal cord stimulation", Journal of Neural Engineering, Jan. 19, 2011, pp. 1741-2560, vol. 8.
Sankarasubramanian, V., et al., "Staggered Transverse Tripoles With Quadripolar Lateral Anodes Using Percutaneous and Surgical Leads in Spinal Cord Stimulation", Neurosurgery, Mar. 2013, pp. 483-491, vol. 72, No. 3.
Smith, Marion C., et al., "Topographical Anatomy of the Posterior Columns of the Spinal Cord in Man: The Long Ascending Fibres", Brain, Sep. 1, 1984, pp. 671-698, vol. 107.
Struijk, Johannes J., et al., "Excitation of Dorsal Root Fibers in Spinal Cord Stimulation: A Theoretical Study", IIEEE Transactions on Biomedical Engineering, Jul. 1993, pp. 632-639, vol. 40, No. 7.
Szarowski, D.H., et al., "Brain responses to micro-machined silicon devices", Brain Research, Sep. 5, 2003, pp. 23-35, vol. 983.
Tschirhart, Craig E., et al., "Biomechanics of vertebral level, geometry, and transcortical tumors in the metastatic spine", Journal of Biomechanics, 2007, pp. 46-54, vol. 40.
Tuch, David S., et al., "Conductivity tensor mapping of the human brain using diffusion tensor MRI", PNAS: Proceedings of the National Academy of Sciences of the United States of America, Sep. 25, 2001, pp. 11697-11701, vol. 98, No. 20.
Wesselink, Wilbert A., et al., "Estimation of Fiber Diameters in the Spinal Dorsal Columns from Clinical Data", IEEE Transactions on Biomedical Engineering, Nov. 1998, pp. 1355-1362, vol. 45, No. 11.
Ko, Hyun-Yoon, et al., "Gross quantitative measurements of spinal cord segments in human", Spinal Cord, 2004, pp. 35-40, vol. 42.
Holsheimer, Jan, et al., "Analysis of Spinal Cord Stimulation and Design of Epidural Electrodes by Computer Modeling", Neuromodulation: Technology at the Neural Interface, 1998, pp. 14-18, vol. 1, No. 1.
CIPO, Examination report for Canadian Patent Application No. 2,958,218, dated Nov. 23, 2017.

* cited by examiner

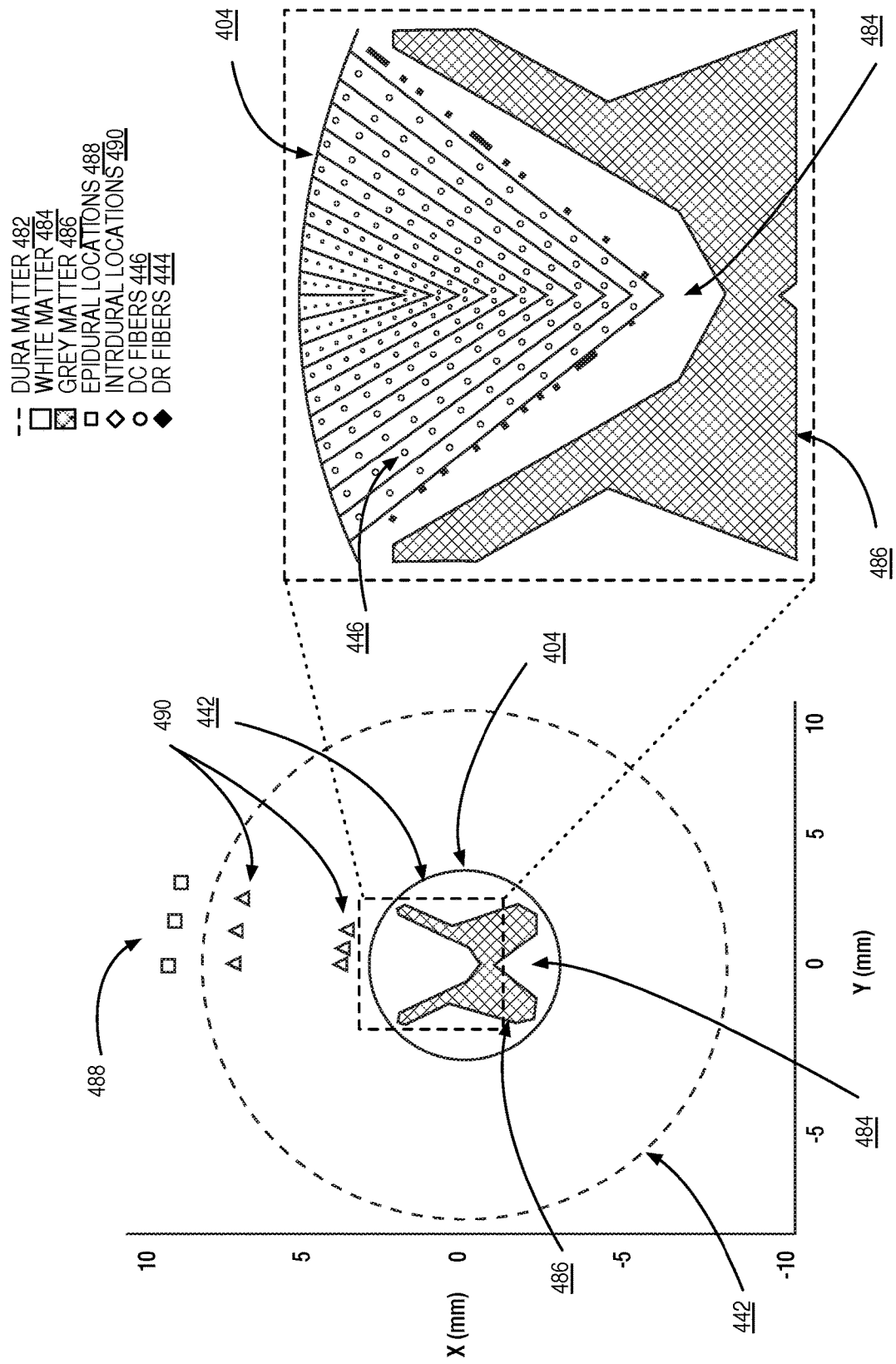

SYSTEMS AND METHODS FOR UTILIZING MODEL-BASED OPTIMIZATION OF SPINAL CORD STIMULATION PARAMETERS

RELATED APPLICATIONS

This application claims priority to PCT Patent Application No. PCT/US16/37571 filed on Jun. 15, 2016 and entitled "SYSTEMS AND METHODS FOR UTILIZING MODEL-BASED OPTIMIZATION OF SPINAL CORD STIMULATION PARAMETERS", which claims priority to U.S. Provisional Patent Application No. 62/183,216 filed on Jun. 23, 2015 and entitled "SYSTEMS AND METHODS FOR UTILIZING MODEL-BASED OPTIMIZATION OF SPINAL CORD STIMULATION PARAMETERS". The Provisional patent Application is incorporated by reference herein in its entirety.

TECHNICAL FIELD

The present disclosure relates to the technical field of spinal cord stimulation in humans for the medical treatment of pain.

BACKGROUND

Many humans suffer from chronic pain conditions such as low back and limb pain, ischemic limb pain, angina, and pain from peripheral neuropathy. One method of treating these conditions includes spinal cord stimulation. The efficacy of spinal cord stimulation is effected by electrode placement, electrode configuration (i.e., the selection of which contacts on the electrode array are active), and the parameters of stimulation including stimulation amplitude (voltage or current), stimulation pulse duration, and stimulation pulse repetition rate (frequency).

SUMMARY OF THE DISCLOSURE

Spinal cord stimulation (SCS) is a common therapy for treating chronic pain, where an implanted pulse generator 106 delivers electrical pulses to an electrode array 102 placed in the epidural/extradural space (FIG. 1A). SCS is FDA-approved for treating chronic low back and limb pain and is currently being investigated for other chronic pain conditions, including ischemic limb pain, angina, and pain from peripheral neuropathy. SCS is based on the gate-control theory of pain, where activation of cutaneous ($A\beta$) nerve fiber collaterals in the posterior/dorsal column (DC) of the spinal cord synaptically inhibit projection neurons in the dorsal horn, thereby preventing transmission of pain-related information to the brain. Activation of DC fibers in the dermatomes associated with pain is often limited by the onset of discomfort. Since discomfort is associated with activation of nearby $A\beta$ fibers in the dorsal roots (DR), successful SCS depends on selective activation of DC fibers without activation of DR fibers.

However, the optimal or even appropriate approach to activate DC fibers without activation of DR fibers is not clear. The distribution of DC and DR fibers directly activated in response to stimulation is determined by the following: the electrode array (synonymous with lead) and its design specifications (i.e., geometry and materials determined by the manufacturers), the location of the electrode array 102 in the extradural space (determined by physician at time of implant, although subject to movement over time and dynamic changes with posture), and the selection of which electrodes 132/contacts on the lead (electrode array) 104 are active and at what amplitude (determined by clinical programming based upon patient sensation and feedback). There are millions of possible stimulation parameters, as well as variations in patient anatomy; thus programming is a time consuming and expensive process with no assurances that the resulting stimulation parameters are optimal.

The present invention disclosure provides a novel approach based on patient-specific computational modeling, to select stimulation parameters, including lead (electrode array) geometry and configuration lead location, and the selection of contacts on the lead 104 that are active and at what amplitude. This approach is expected to reduce the time required to select parameters for effective treatment and to increase the treatment efficacy.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One approach is to use a computational method to optimize patient-specific parameters (inputs) for spinal cord stimulation, which is summarized as follows: construct a patient-specific electrical model of a patient's spinal cord and surrounding tissues; define inputs to the patient-specific electrical model; determine a distribution of a plurality of electrical stimuli for a given patient-specific model; determine which residing neural elements (for example dorsal column axons, dorsal root axons, neurons within the spinal cord, and neurons within the dorsal root ganglia) are directly activated based on the application of the distribution of the plurality of electrical stimuli from the patient-specific model; define a cost function result based on the electrical stimuli applied and the neural element activations achieved; and adjust the inputs to the patient-specific electrical model so that the cost function is reduced (until a minimum is achieved). Other embodiments of this aspect include corresponding computer systems, apparatus, and computer programs recorded on one or more computer storage devices, each configured to perform the actions of the methods.

Other embodiments of this aspect include corresponding computer systems, apparatus, and computer programs recorded on one or more computer storage devices, each configured to perform the actions of the methods.

BRIEF DESCRIPTION OF THE DRAWING FIGURES

The accompanying drawing figures incorporated in and forming a part of this specification illustrate several aspects of the disclosure, and together with the description serve to explain the principles of the disclosure.

Figure 1C:
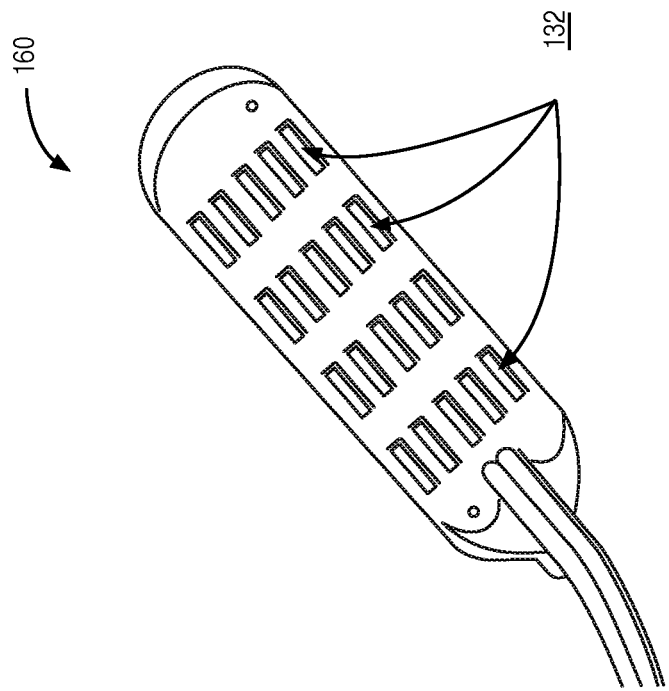
Figure 1B:
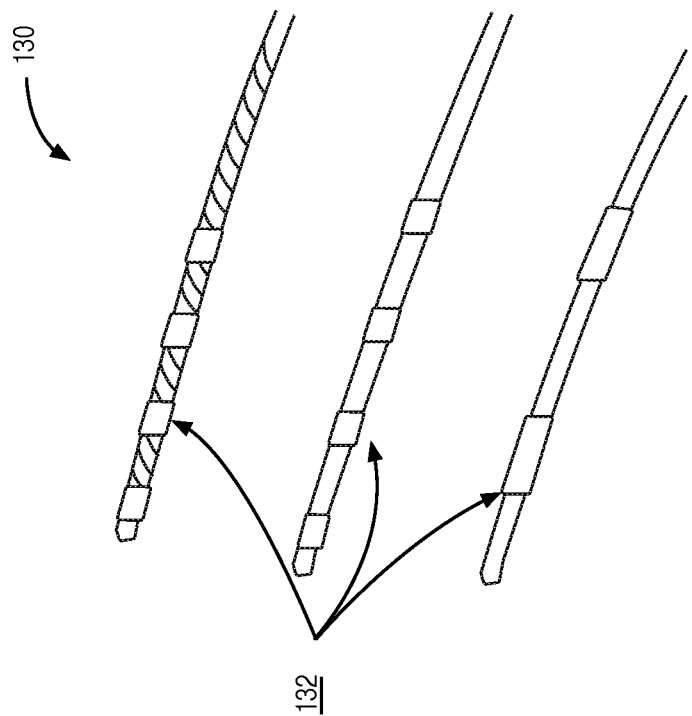
Figure 2:
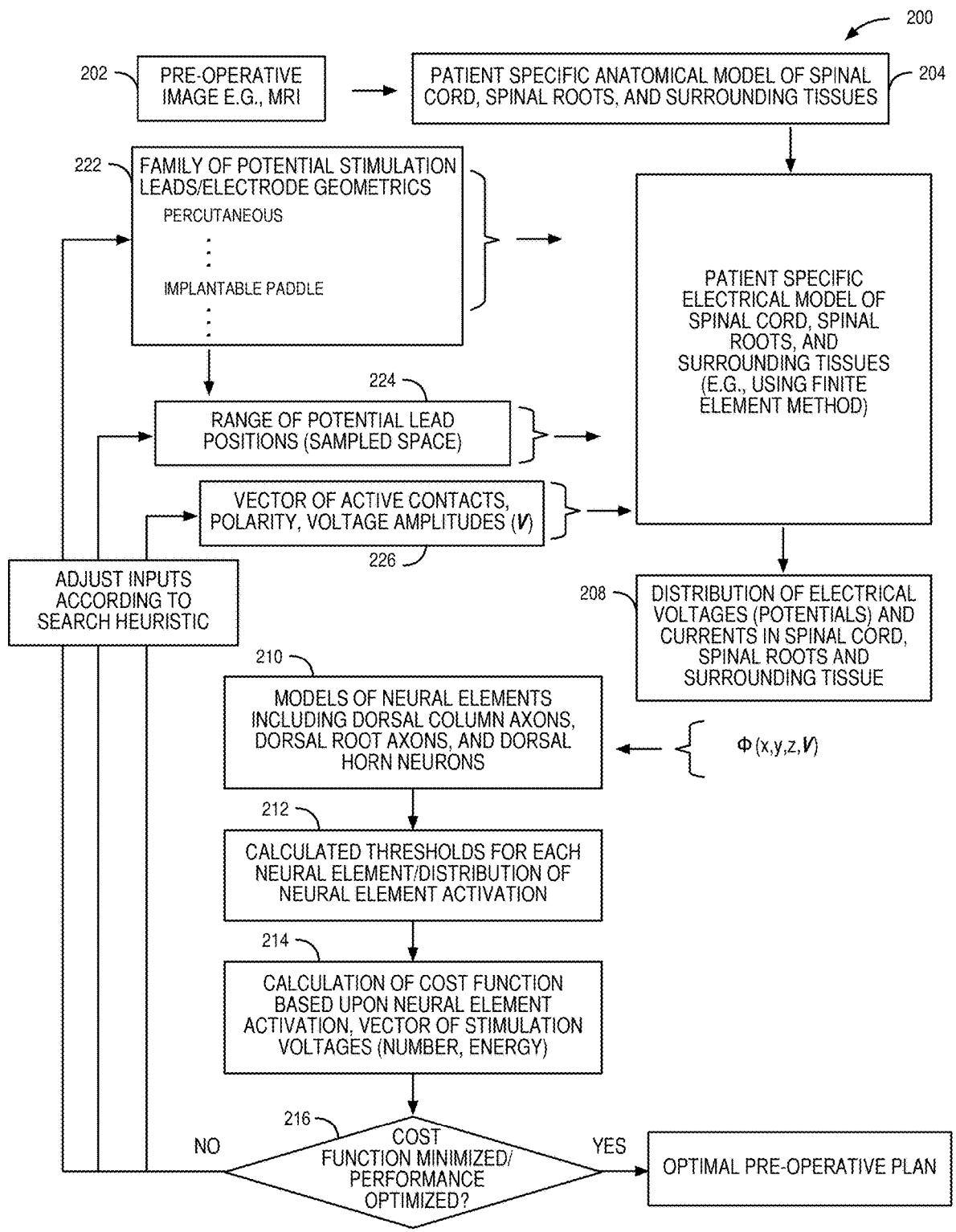
Figure 3:
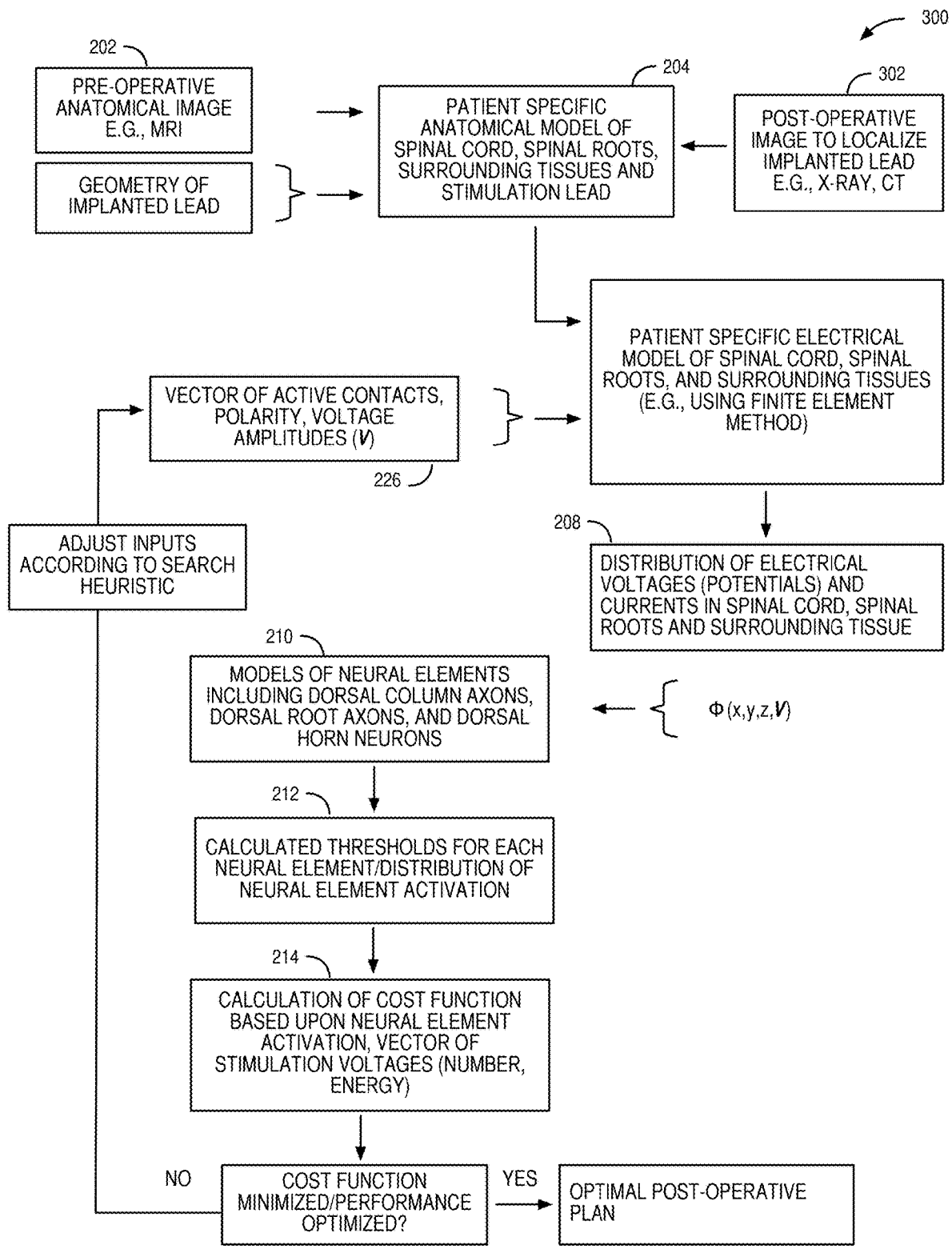
Figure 4A:
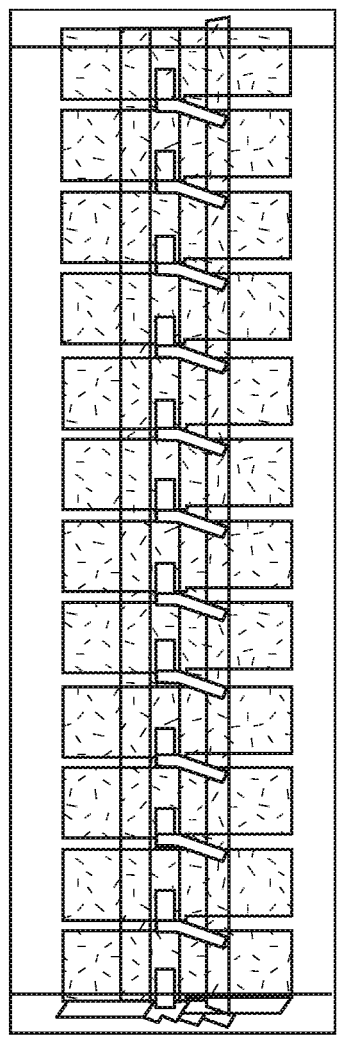
Figure 4B:
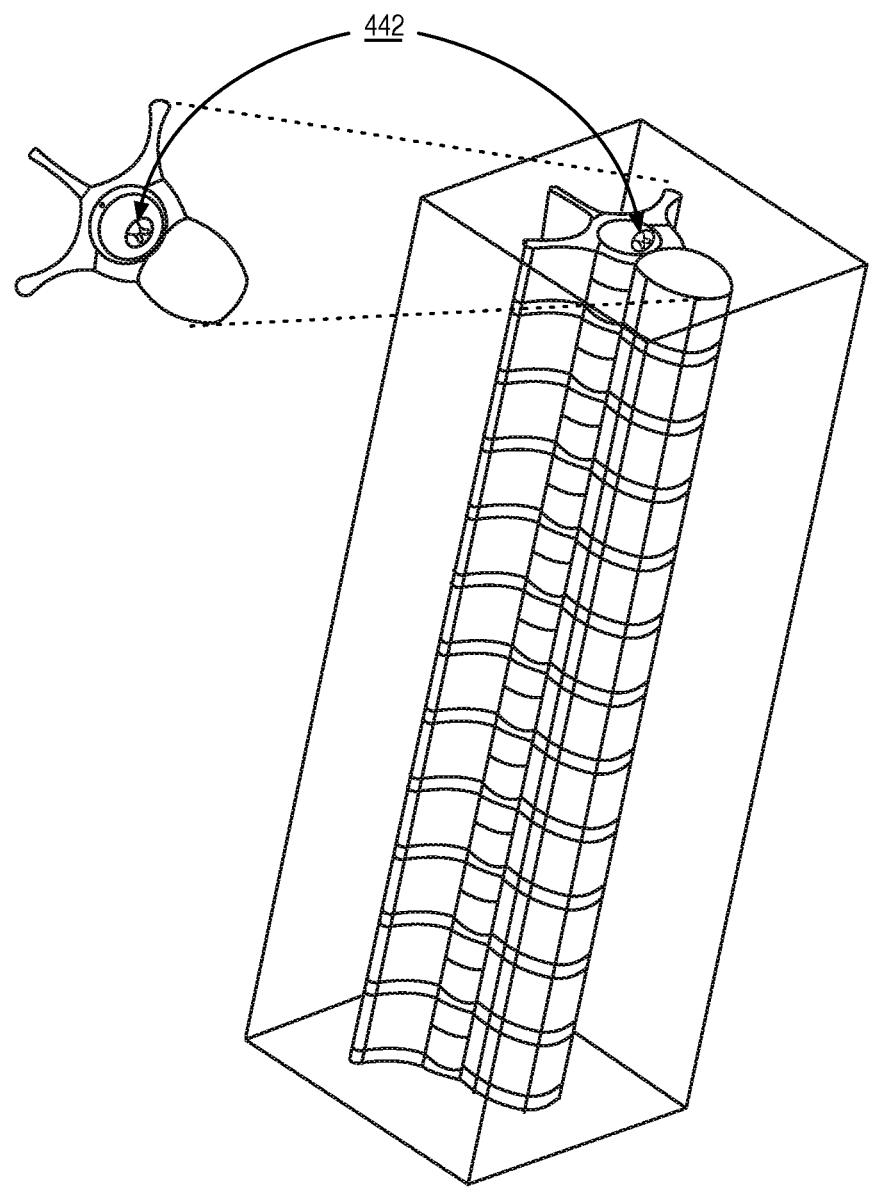
Figure 4C:
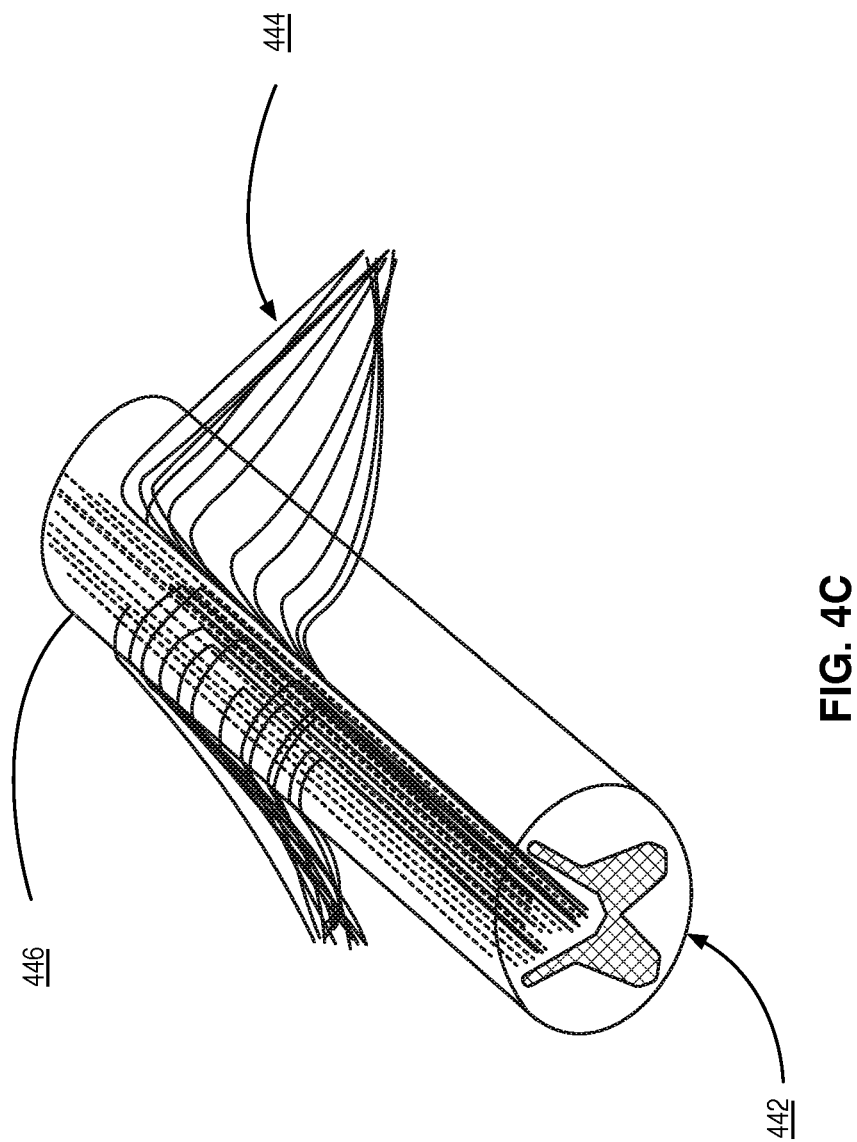
Figure 5:
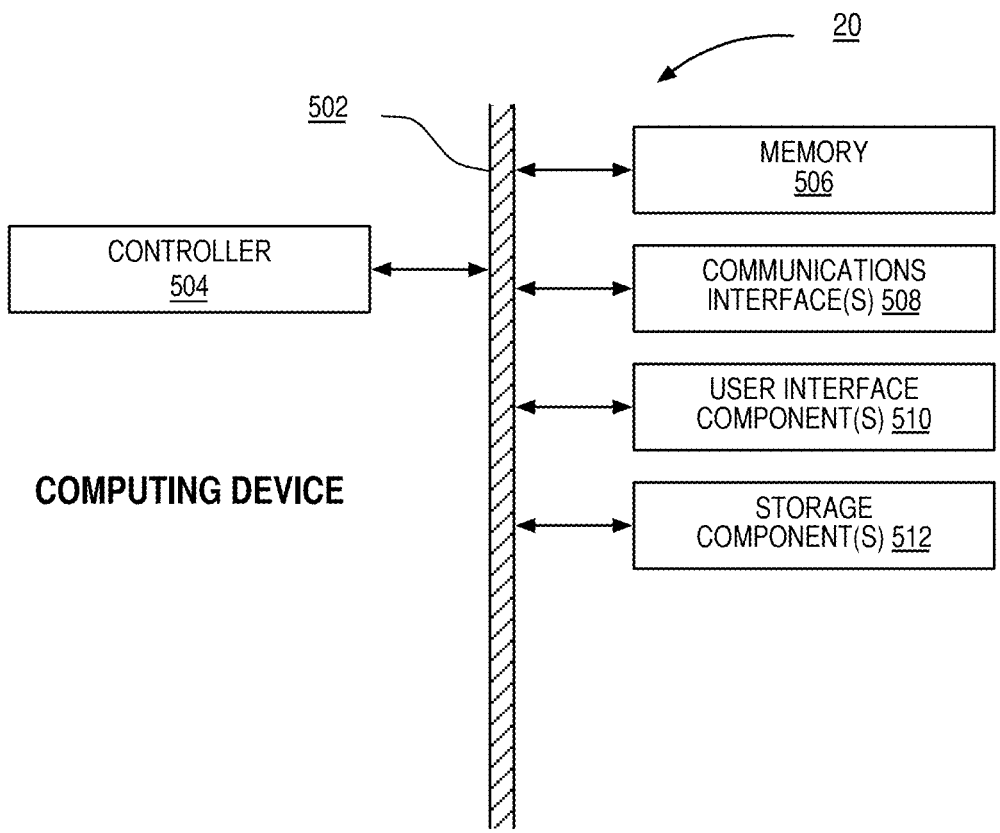
Figure 6:
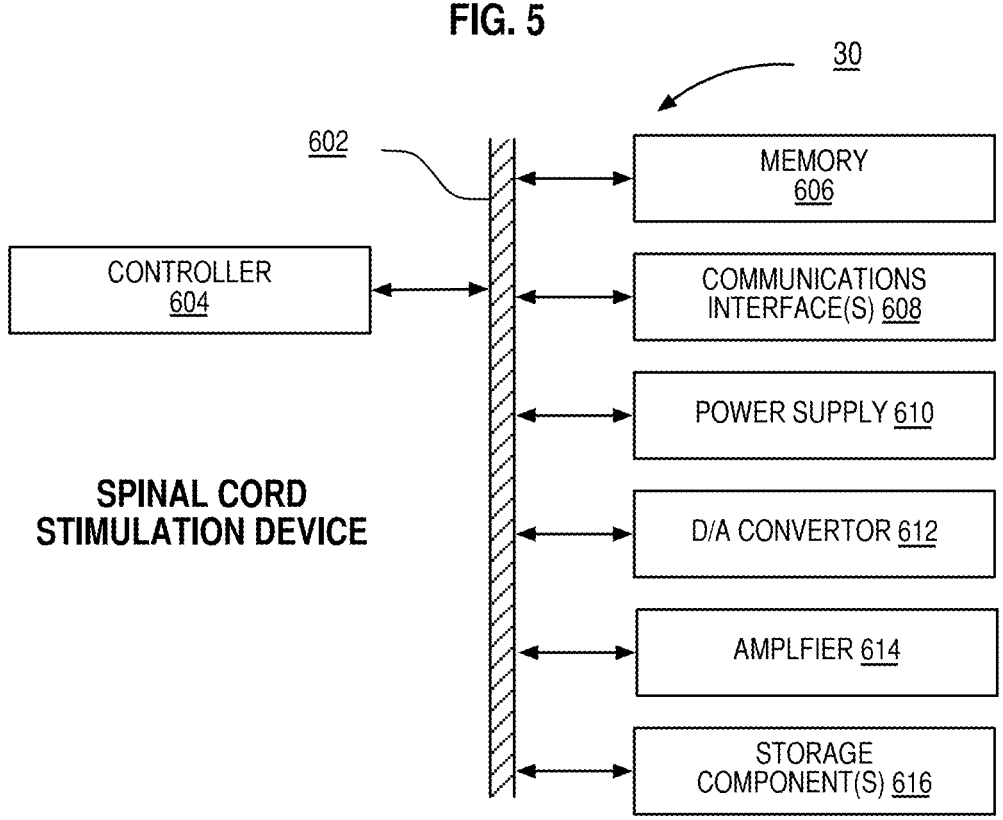

FIG. 1A graphically illustrates an example of an implanted spinal cord stimulation device;

FIG. 1B graphically illustrates an percutaneous electrode array;

FIG. 1C graphically illustrates an percutaneous electrode array;

FIG. 2 graphically illustrates a pre-operative planning process for electrode targeting and selection according to some embodiments of the present disclosure;

FIG. 3 graphically illustrates a pre-operative planning process for electrode selection and targeting according to some embodiments of the present disclosure;

FIG. 4A graphically illustrates a view of a three-dimensional model of the spine according to some embodiments of the present disclosure;

FIG. 4B graphically illustrates another view of the three-dimensional model of the spine according to some embodiments of the present disclosure;

FIG. 4C graphically illustrates a view of the trajectories of modeled dorsal column and dorsal root fibers; and FIG. 4D graphically illustrates locations, relative to the spinal cord and dura, where a percutaneous electrode array can be used to stimulate passing axons according to some embodiments of the present disclosure;

FIG. 4E graphically illustrates a distribution of dorsal column and dorsal root fibers within the dorsomedial white matter of a spinal cord according to some embodiments of the present disclosure;

FIG. 5 is a block diagram of a computing device according to some embodiments of the present disclosure; and FIG. 6 is a block diagram of a spinal simulation device according to some embodiments of the present disclosure.

DETAILED DESCRIPTION

The present disclosure is described with specificity to meet statutory requirements. However, the description itself is not intended to limit the scope of this patent. Rather, the inventors have contemplated that the claimed subject matter might also be embodied in other ways, to include different steps or elements similar to the ones described in this document, in conjunction with other present or future technologies. Moreover, although the term "step" may be used herein to connote different aspects of methods employed, the term should not be interpreted as implying any particular order among or between various steps herein disclosed unless and except when the order of individual steps is explicitly described.

Throughout this specification, like reference numbers signify the same elements throughout the description of the figures.

When elements are referred to as being "connected" or "coupled", the elements can be directly connected or coupled together, or one or more intervening elements may also be present. In contrast, when elements are referred to as being "directly connected" or "directly coupled," there are no intervening elements present.

The subject matter may be embodied as devices, systems, methods, and/or computer program products. Accordingly, some or all of the subject matter may be embodied in hardware and/or in software (including firmware, resident software, micro-code, state machines, gate arrays, etc.) Furthermore, the subject matter may take the form of a computer program product on a computer-usable or computer-readable storage medium having computer-usable or computer-readable program code embodied in the medium for use by or in connection with an instruction execution system. In the context of this document, a computer-usable or computer-readable medium may be any medium that can contain, store, communicate, propagate, or transport the program for use by or in connection with the instruction execution system, apparatus, or device.

The computer-usable or computer-readable medium may be for example, but not limited to, an electronic, magnetic, optical, electromagnetic, infrared, or semiconductor system, apparatus, device, or propagation medium. By way of example, and not limitation, computer-readable media may comprise computer storage media and communication media.

Computer storage media is non-transitory and includes volatile and nonvolatile, removable and non-removable media implemented in any method or technology for storage of information such as computer-readable instructions, data structures, program modules, or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage components, or any other medium which can be used to store the desired information and may be accessed by an instruction execution system. Note that the computer-usable or computer-readable medium can be paper or other suitable medium upon which the program is printed, as the program can be electronically captured via, for instance, optical scanning of the paper or other suitable medium, then compiled, interpreted or otherwise processed in a suitable manner if necessary, and then stored in computer memory.

Communication media typically embodies computer-readable instructions, data structures, program modules or other data in a modulated data signal such as a carrier wave or other transport mechanism and includes any information delivery media. The term "modulated data signal" can be defined as a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above-mentioned should also be included within the scope of computer-readable media.

When the subject matter is embodied in the general context of computer-executable instructions, the embodiment may comprise program modules, executed by one or more systems, computers, or other devices. Generally, program modules include routines, programs, objects, components, and data structures (and the like) that perform particular tasks or implement particular abstract data types. Typically, the functionality of the program modules may be combined or distributed as desired in various embodiments.

Recitation of ranges of values herein are merely intended to serve as a shorthand method of referring individually to each separate value falling within the range, unless otherwise indicated herein; and each separate value is incorporated into the specification as if it were individually recited herein. Therefore, any given numerical range shall include whole and fractions of numbers within the range. For example, the range "1 to 10" shall be interpreted to specifically include whole numbers between 1 and 10 (e.g., 1, 2, 3, . . . 9) and non-whole numbers (e.g., 1.1, 1.2, . . . 1.9).

Although process (or method) steps may be described or claimed in a particular sequential order, such processes may be configured to work in different orders. In other words, any sequence or order of steps that may be explicitly described or claimed does not necessarily indicate a requirement that the steps be performed in that order unless specifically indicated. Further, some steps may be performed simultaneously despite being described or implied as occurring non-simultaneously (e.g., because one step is described after the other step) unless specifically indicated. Where a process is described in an embodiment, the process may operate without any user intervention.

For the purposes of promoting an understanding of the principles of the present disclosure, reference will now be made to preferred embodiments, and specific language will be used to describe the same. It will nevertheless be understood that no limitation of the scope of the disclosure is thereby intended; such alteration and further modifications of the disclosure, as illustrated herein, is being contemplated as would normally occur to one skilled in the art to which the disclosure relates.

Articles "a" and "an" are used herein to refer to one or to more than one (i.e. at least one) of the grammatical object of the article. By way of example, "an element" means at least one element and can include more than one element.

Unless otherwise defined, all technical terms used herein have the same meaning as commonly understood by one of ordinary skill in the art to which this disclosure belongs.

The present disclosure provides, in part, a novel approach based on patient-specific computational modeling to select stimulation parameters; including lead geometry, lead (electrode array) 104 location, and the selection of contacts on the lead (electrode array) 104 that are active and at what amplitude (voltage or current magnitude and polarity). The inventors have previously developed and validated a computational model of SCS that closely predicts the stimulation thresholds measured intra-operatively during surgery in human subjects. The systems and methods described herein demonstrate how to use this model for selection of optimal parameters of spinal cord stimulation (FIGS. 2 and 3). The parameter selection process is accomplished through model-based optimization, using a rigorous mathematical approach with a defined cost function, rather than trial-and-error experimentation. This approach is expected to reduce the time required to select stimulation parameters for effective treatment and to increase the treatment efficacy.

Referring now to FIG. 1A, a graphical illustration of an implanted spinal cord stimulation device is shown. The implanted spinal cord stimulation device 30 is comprised of an electrode array 102, lead wires 104, and an implantable pulse generator 106. Computational modeling has been used as a tool for SCS device design, but model-based optimization has not been described as an approach to selection of stimulation parameters. Referring now to FIGS. 1B and 1C, modeling studies have shown that percutaneous arrays 130 in longitudinal (rostral-caudal) bipolar and tripolar configurations, and paddle arrays 160 in transverse (medial-lateral) tripolar configurations outperform monopolar configurations in selective activation of the targets of SCS, the dorsal column (DC) fibers, over the undesirable targets, the dorsal root (DR) fibers. However, other than a couple of studies looking at optimal geometry and spacing of electrodes in a longitudinal bipolar and tripolar configuration; lead design (geometry), lead (electrode array) placement, and selection of stimulation parameters has been largely a trial-and-error process. Trial-and-error experimentation is not an efficient approach and is unlikely to lead to an optimal result, as the efficacy of SCS depends on the geometry, polarity, and location of the stimulation electrodes. Therefore, we invented model-based optimization to improve SCS parameter selection.

A numerical process (e.g., a genetic algorithm or other search heuristic) is used in an iterative manner to identify optimal stimulation parameters, including lead (electrode array) geometry, location, and the selection of contacts that are active and at what amplitude (voltage or current magnitude and polarity). The process relies on a cost function that is minimized through the numerical optimization process. This cost function seeks to increase the selectivity of SCS in targeting DC fibers over DR fibers and/or to reduce the total electrical energy required for stimulation. These two components can be differentially weighted to obtain stimulation parameters, including lead geometry, lead location, and the selection of contacts on the lead that are active and at what amplitude, that optimize selectivity (i.e., the ratio of active DC fibers to active DR fibers) and efficiency (i.e., the total electrical energy required to activate DC fibers) to different degrees. Other cost functions that include consideration of activation of other residing neural elements including dorsal column axons, dorsal root axons, neurons within the spinal cord, and neurons within the dorsal root ganglia, and other aspects of performance including stimulation energy, stimulation charge, and stimulation power are also contemplated.

Previous approaches have included clinical programming of stimulation parameters; however, these trial-and-error methods did not rely on or disclose either patient-specific computational models or the use of mathematical optimization methods.

The Optimization Process

Referring now to FIG. 2 and FIG. 3, the optimization process begins by calculating the electric potentials generated during SCS. This is done by constructing a three-dimensional, patient-specific volume conductor model of the implanted electrode array, spinal cord, and surrounding regions/anatomical structures, including the dura and arachnoid maters lumped into a single ellipsoidal shell, cerebral spinal fluid, vertebrae, intervertebral disks, fat in the epidural space, and a lumped circumscribing region of soft tissue. The dimensions of the aforementioned regions/structures and their relative distances with respect to each other are obtained from the patient's medical images, which include any images, including magnetic resonance (MR), computed tomography (CT) or X-ray images that are acquired before (preoperative) or after (postoperative) the electrode array 102 is implanted, as well as postoperative X-ray, computed tomography (CT) images or magnetic resonance (MR) images. The spinal cord and surrounding structures/regions are placed inside of a circumscribing rectangular prism (100 mm×100 mm×300 mm) of homogeneous, isotropic soft tissue that is large enough to behave as an infinite conductive medium (FIGS. 4A-4E). Spinal dimensions that cannot be determined from the medical images are chosen so that they are consistent with those of an adult human lower thoracic/upper lumber spine. Neural tissue can be approximated as primarily resistive for typical SCS parameters; therefore, all tissues are modeled as purely conductive with electrical properties taken from published data. Modeled electrode arrays are placed either within the extradural or intradural space of the spine, and the potentials generated by the electrode array are calculated by using the finite element method (FEM) to approximate the solution to Laplace's equation (Equation 1) in the modeled domain:

$$\nabla \cdot (\Sigma(x,y,z) \cdot \nabla \Phi) = 0 \quad (1)$$

Where, $\Sigma(x,y,z)$ is a tensor field that specifies the conductivity throughout the entire volume conductor.

The next step in the optimization process is simulating the response of cable models of DC and DR fibers to the electric potentials calculated with the volume conductor model 208. The dorsomedial white matter 484 of the cord (i.e., between the dorsal boundaries of the cord and grey matter 486) is split into multiple dermatomes based on the mediolateral segmental lamination of DC fibers. 20 DC fibers 446 are bilaterally distributed (10 on either side of the transverse midline) within the 10 most medial dermatomes, for a total of 200 DC fibers—that originate from distal, caudal DR fibers 444, which are not modeled. An additional 200 DC fibers are bilaterally distributed in the lateral-most dermatome, but these fibers are attached to the proximal end of 200 corresponding DR fibers. DR fibers descend about the dorsal aspect of the spinal cord in a ventrolateral direction (i.e., via the rootlets) and exit the spine through the intervertebral foramina. An illustration of the above is shown in FIGS. 4A-4E.

The diameters of myelinated fibers in the dorsomedial white matter 484 range between 1-15 μm. Although the vast majority (>60%) of the fibers have diameters between 1-6 μm, computational modeling studies have shown that the predicted thresholds of the larger diameter fibers (~12 μm) are closest to clinically measured stimulation thresholds in SCS. Therefore, we chose a fiber diameter of 9 μm for both the DC fibers 444 and DR fibers 446. The DC fibers and DR fibers were stimulated with a 300 μs monophasic rectangular pulse, consistent with typical pulse widths (175-600 μs) used in SCS. Because the electrical properties of the conductive medium are not dependent on the electric potentials (i.e., $\Phi$), the form of Laplace's equation solved is linear, and thus, the potentials at a given stimulus amplitude are calculated by multiplying the FEM solution by a scalar. The stimulation threshold voltage for each fiber is calculated using a bisection process (relative error <1%), and input-output curves of the activated population as a function of the stimulation amplitude/power are constructed. 212

The final step in the optimization process is using the results from the coupled FEM and cable models to evaluate 214 and minimize a cost function 216 via a numerical optimization process. We propose using a genetic process (GA), although other search heuristics (e.g., simulate annealing, swarm optimization) could also be used. For a given lead configuration, and lead position, the GA will begin with a population of 20 randomly generated parameter sets defining the configuration or selection of contacts on the lead that are active and at what amplitude (voltage or current magnitude and polarity). The performance of each configuration will be assessed. Stimulation selectivity will be quantified by constructing a curve, p(x), of the proportion of a non-target population, the DR fibers 444, activated versus selected proportions of a target population, the DC fibers 446, and calculating the area (Equation 2) under the curve:

$$A = \int p(x) dx. \quad (2)$$

Stimulation efficiency will be quantified by calculating the electrical energy (Equation 3) consumed by the stimulation pulse in activating the target DC fibers, $$E = \int I(t) V(t) dt \quad (3)$$

where I and V are the waveforms of the applied stimulation voltage and current, respectively, over time. The cost of each set of stimulation parameters, including lead geometry, lead location, and the selection of contacts on the lead that are active and at what amplitude will be a differentially weighted linear combination of A and E, with the cost given by Equation 4.

$$\text{Cost} = C1 * A + C2 * E \quad (4)$$

C1 and C2 are scaling/weighting coefficients that determine the relative contributions of efficacy, A, and efficiency, E, to the cost function and eventual performance. Other cost functions combining functions of efficacy and efficiency with differential weighting are also possible.

After the initial fitness evaluation, each subsequent generation will consist of the 2 fittest solutions from the previous generation and 18 new solutions created through genetic recombination of 18 different pairs of solutions from the previous generation, where more fit solutions have a higher probability of being represented in these crossings. The GA will terminate when the average change in the cost function is <0.1% over 100 generations.

Preoperative model-based optimization 200 is conducted offline, before the patient is implanted with the SCS device (FIG. 2). First, preoperative T1-weighted (T1W) MR, T2-weighted (T2W) MR, and CT images 202 are used to construct a patient-specific model 204 of the spine and surrounding area. All images are co-registered to a common space, and the images are processed using image-processing software. The images are registered to an anatomical atlas of the spine using a 12-parameter affine transformation, and the inverse of the resultant mapping is used to define volumes for the grey and white matter of the spinal cord, the boundary of the dura mater, and the volumes of other surrounding regions, such as the vertebrae and intervertebral disks. The electrical properties of the spinal cord and surrounding regions are defined based upon experimental measurements of tissue properties as reported in the scientific or clinical literature. The trajectories of the DC fibers 446 and DR fibers 444 are determined by constructing splines that follow the trajectory of the gracile fasciculus, which is defined using a co-registered anatomical atlas of the spine; or alternatively, trajectories are defined by conducting deterministic or probabilistic tractography on diffusion MR images of the patient.

Next, the patient-specific model is coupled with a numerical optimization process (e.g., genetic algorithm) to determine the optimal electrode array (or lead) design 210. The type of lead is selected from different electrode designs available from different manufacturers, such as cylindrical/percutaneous arrays and planar/paddle arrays 222, and the process minimizes the cost function (Equation 4) by altering the following characteristics: the number, size, shape, and distribution of individual electrode contacts; the optimal electrode position/location 224; and the selection of contacts on the lead that are active and at what amplitude 226. Optimal solutions are those that use as little energy (Equation 3) as possible to activate the target DC fibers 212 with minimal co-activation of DR fibers and/or non-target DC fibers (Equation 2).

Referring now to FIG. 3, offline model-based optimization of the stimulation parameters can also be carried out post-operatively 300 throughout the course of the therapy (FIG. 3). This is advantageous because the tissue response to the lead (e.g., scarring and edema) and the movement of the lead in the epidural space can have an effect on the optimal electrode configuration 326. First, post-operative imaging 302 is used to assess the tissue response, its effect on the position of the spinal cord and lead, and the extent to which the implanted lead 302 has moved. Next, the post-operative imaging data is used to update the patient-specific model and the numerical optimization process is used to determine if a more optimal solution exists. If a more optimal electrode configuration does not exist, the optimization process can be run again to assess the prospective benefits of a revision surgery to reposition or replace the lead.

Referring now to FIG. 4A, the three-dimensional model of the spine is comprised of vertebra, intervertebral disks, a dorsal column, and a spinal cord 442.

Referring now to FIG. 4B, in another view of the three-dimensional model of the spine, the model is comprised of the vertebra, the dorsal column, the spinal cord 442, and additionally grey matter.

Referring now to FIG. 4C, populations of dorsal column and dorsal root fibers in the spinal cord 442, the DC Fibers 446, and the DR Fibers 444.

Referring now to FIG. 4D, the spinal cord and potential location of the implanted percutaneous electrode array is comprised of the spinal cord 442, white matter 484, grey matter 486, the dorsal column 404, epidural locations 488, and intradural locations 490.

Referring now to FIG. 4E the dorsal column fiber and dorsal root fiber distribution and placement within dorsomedial white matter of a spinal cord is comprised of DC Fibers 446, a dorsal column 404, white matter 484, and grey matter 486.

FIG. 5 is a block diagram of a computing device according to one embodiment of the present disclosure. As illustrated, the computing device 20 includes a controller 504 connected to memory 506, one or more communications interfaces 508, one or more user interface components 510, and one or more storage components 512, by a bus 502 or similar mechanism. The controller 504 is a microprocessor, digital ASIC, FPGA, or the like. In general, the computing device 20 includes a control system having associated memory 506. In some embodiments, the controller 504 is a microprocessor, and the optimization modules are implemented in software and stored in the memory 506 for execution by the controller 504. However, the present disclosure is not limited thereto. The aforementioned functions and module may be implemented in software, hardware, or a combination thereof. The computing device 20 also includes a communication interface 508 enabling the computing device 20 to connect to a network. The one or more user interface components 510 may include, for example, a touchscreen, a display, one or more user input components (e.g., a keypad), a speaker, or the like, or any combination thereof. The storage component(s) 512 is a non-volatile memory. However, the present invention is not limited thereto.

FIG. 6 is a block diagram of a spinal cord stimulation device 30 according to one embodiment of the present disclosure. As illustrated, the spinal cord stimulation device 30 includes a controller 604 connected to memory 606, one or more communications interfaces 608, a power supply 610, a D/A convertor 612, an amplifier 614, and one or more storage components 616, by a bus 602 or similar mechanism. The controller 604 is a microprocessor, digital ASIC, FPGA, or the like. In general, the spinal cord stimulation device 30 includes a control system having associated memory 606. In some embodiments, the controller 604 is a microprocessor, and the spinal cord stimulation modules are implemented in software and stored in the memory 606 for execution by the controller 604. However, the present disclosure is not limited thereto. The aforementioned functions and modules may be implemented in software, hardware, or a combination thereof. The spinal cord stimulation device 30 also includes a communication interface 608 enabling the spinal cord stimulation device 30 to receive updated/optimized parameters. The power supply is typically a battery. The D/A convertor 612 operates to convert the electrical signals from digital to analog for subsequent amplification by the amplifier 614 and attachment to the electrodes. The storage component(s) 616 is a non-volatile memory operable to store updated/optimized parameters. However, the present invention is not limited thereto.

Example Usage

Five SCS models of patients that had undergone acute intraoperative evaluation of extradural and intradural SCS were constructed. The geometries of the spinal cord and dural sac, as well as the position of the cord within the dural sac, were obtained from the pre-operative MR images of the corresponding patients. The geometry of the spinal column did not vary across patients and reflected the geometry of an average adult human lower thoracic/upper lumbar spine. Similar to what was done clinically, SCS was administered by delivering 300 μs current pulses with a percutaneous electrode array (lead) in a bipolar electrode configuration, where the cathode was proximal to T8 and the anode was rostral to the cathode. Clinical sensory thresholds (i.e., when the patient first reported a paresthesia) were compared against theoretical sensory thresholds (i.e., the lowest threshold amongst modeled DC fibers and DR fibers) to assess the predictive capabilities of the SCS model. The computational model predicted the relative order of the stimulation thresholds, the greater than five-fold difference between extradural and intradural stimulation thresholds, and the effect of the cord position on the stimulation thresholds.

Further computational experiments were conducted to assess the theoretical performance (efficiency and selectivity) of intradural SCS versus extradural SCS and how sensitive the performance of SCS was to variability in the electrode position and patient geometry. This was accomplished by analyzing the results of each patient-specific model at nine different electrode locations: three epidural locations 488 one mm above the dura, three intradural locations 490 one mm below the dura, and three intradural locations one mm above the cord, with the three points in each of the above sets having lateral (clockwise) offsets of 0°, 10°, and 20° from the transverse midline, respectively.

The results show that efficiency of SCS was less sensitive to variations in the spinal geometry of the patient but more sensitive to the location of the lead.

Selectivity was sensitive to the position of the lead. For both epidural and intradural SCS, better selectivity (i.e., activation of DC fibers without co-activation of DR fibers) was achieved when the lead was positioned medially along the transverse midline of the cord; however, between the two, the best selectivity was achieved with intradural SCS. For example, 25% and 50% of the DC fibers could be activated before the first DR fiber was activated with extradural SCS and intradural SCS, respectively. However, as the lead was laterally displaced from the midline, the advantage gained in selectivity with intradural SCS declined. Therefore, in general, there is a tradeoff between selective activation of more lateral dermatomes and selectivity—or broad pain coverage.

As a final analysis, computational experiments were conducted to determine if novel electrode designs could be used to increases the performance of SCS. In this analysis, we tested 5 different electrode configurations: 2 Medtronic percutaneous leads, Models 3776/3876 and 3778/3878 (Medtronic Inc., Minneapolis, Minn.), in longitudinal tripolar (LT) configurations; the Saint Jude Medical Penta™ (St. Jude Medical, Saint Paul, Minn.) in 2 different transverse tripolar (TT) configurations; and our own novel design, a percutaneous azimuthal array in an angular tripolar (AT) configuration. All tested configurations had better selectivity when placed within the intradural space. The TT had better pain coverage than the LT in selectively activating DC fibers over DR fibers, and the AT had had better pain coverage than the TT—but at the expense of higher energy consumption. These results demonstrate the advantage of an optimization process to select preoperatively appropriate or optimal electrode models, and that such optimization can increase the performance of SCS.

The next step, as described in the current application, is to couple the computational model of SCS with an optimization algorithm and identify optimal stimulation parameters, including lead type (or geometry), lead (electrode array) location, and the selection of contacts on the lead (electrode array) that are active and at what amplitude (voltage or current magnitude and polarity). The process relies on a cost function that is minimized through the numerical optimization process. This cost function seeks to increase the selectivity of SCS in targeting DC fibers over DR fibers as well as to reduce the total electrical energy required for stimulation.

Those skilled in the art will recognize improvements and modifications to the embodiments of the present disclosure. All such improvements and modifications are considered within the scope of the concepts disclosed herein and the claims that follow.

What is claimed is:

1. A computer implemented method of optimizing patient-specific parameters for spinal cord stimulation comprising:
    determining a patient-specific electrical model using patient-specific medical images, the patient-specific electrical model based on the geometry of a spinal cord and a surrounding area, the spinal cord and the surrounding area together forming a spinal cord area having dimensions obtained from the patient-specific medical images;
    receiving inputs to the patient-specific electrical model, the inputs comprising physical positions of electrodes in the spinal cord area;
    determining a distribution of a plurality of electrical stimuli, the distribution of electric stimuli comprising a vector of active electrode contacts and their respective stimulation amplitudes and polarities;
    determining neural element activations based on an application of the distribution of the plurality of electrical stimuli from the patient-specific electrical model;
    calculating a cost function result, the cost function result based on the electrical stimuli applied and the neural element activations achieved;
    performing a comparison of the cost function result to a cost function threshold; and
    based on the comparison, adjusting the inputs to the patient-specific electrical model.

2. The computer implemented method of claim 1 wherein the patient-specific electrical model further comprises lumped dura and arachnoid maters, vertebrae, intervertebral disks, and a circumscribing soft-tissue region.

3. The computer implemented method of claim 1, wherein the electrical stimuli correspond to a physical placement of electrodes within the spinal cord area.

4. The computer implemented method of claim 3, wherein the electrical stimuli are characterized by voltage amplitudes and polarities.

5. The computer implemented method of claim 3, wherein the electrical stimuli are further characterized by a pulse polarity, pulse width, and inter-pulse interval.

6. The computer implemented method of claim 3, wherein the neural elements comprise dorsal column axons, dorsal root axons, and dorsal horn projection neurons.

7. The computer implemented method of claim 1, wherein determining neural element activations further comprises performing a second comparison of a modeled neural element response to a neural element response threshold.

8. The computer implemented method of claim 1, wherein performing the comparison of the cost function result to the cost function threshold further comprises determining if the cost function has been optimized or determining if the cost function has been minimized.

9. The computer implemented method of claim 1, wherein the method is performed temporally prior to implantation of a spinal cord stimulation apparatus into the spinal cord area.

10. The computer implemented method of claim 9, wherein receiving inputs to the patient-specific electrical model further comprises receiving a preoperative image.

11. The computer implemented method of claim 9, wherein receiving inputs to the patient-specific electrical model further comprises receiving lead configurations, and lead positions.

12. The computer implemented method of claim 11, wherein adjusting inputs to the patient-specific electrical model further comprises adjusting the lead configurations, the lead positions, and the vector of active electrode contacts and their respective stimulation amplitudes and polarities.

13. The computer implemented method of claim 1, wherein the method is performed temporally after implantation of a spinal cord stimulation apparatus into the spinal cord area.

14. The computer implemented method of claim 13, wherein receiving inputs to the patient-specific electrical model further comprises receiving a post-operative image of implanted electrodes or receiving a geometry of implanted electrodes.

15. The computer implemented method of claim 13, wherein adjusting inputs to the patient-specific electrical model further comprises adjusting the vector of active electrode contacts and their respective stimulation amplitudes and polarities.

16. The method of claim 1, wherein determining a patient-specific electrical model using patient-specific medical images comprises using pre-operative patient-specific medical images taken prior to implantation of a spinal cord stimulation device into the spinal cord area.

17. The method of claim 16, wherein using pre-operative patient-specific medical images comprises using weighted pre-operative patient-specific images.

18. A device comprising:
    a hardware processor and memory operable to:
        determine a patient-specific electrical model using patient-specific medical images, the patient-specific electrical model comprising the geometry of a spinal cord and a surrounding area, the spinal cord and the surrounding area together forming a spinal cord area having dimensions obtained from the patient-specific medical images;
        receive inputs to the patient-specific electrical model, the inputs comprising physical positions of electrodes in the spinal cord area;
        determine a distribution of a plurality of electrical stimuli, the distribution of electric stimuli comprising a vector of active electrode contacts and their respective stimulation amplitudes and polarities;
        determine neural element activations based on an application of the distribution of the plurality of electrical stimuli from the patient-specific electrical model;
        calculate a cost function result, the cost function result based on the electrical stimuli applied and the neural element activations achieved;
        perform a comparison of the cost function result to a cost function threshold; and
        based on the comparison, adjust the inputs to the patient-specific electrical model.

19. A system comprising:
    a spinal cord stimulation device comprising:

a hardware processor and memory operable to:
  receive optimized patient specific parameters for spinal cord stimulation;
  store the optimized patient specific parameters for spinal cord stimulation;
  obtain the optimized patient specific parameters from storage;
a D/A convertor associated with the hardware processor and memory, and coupled to an amplifier operable to:
  convert the optimized patient specific parameters to an analog signal;
  amplify the analog signal; and
  transmit the amplified analog signal over a plurality of lead wires to a corresponding plurality of electrodes; and
a device client for optimizing patient specific parameters for spinal cord stimulation operable to:
  determine, using patient-specific medical images, a patient specific electrical model of the geometry of a patient spinal cord area having dimensions obtained from the patient-specific medical images;
  receive inputs to the patient specific electrical model of the patient spinal cord area, the inputs comprising physical positions of electrodes in the spinal cord area;
  determine a distribution of a plurality of electrical stimuli, the distribution of electric stimuli comprising a vector of active electrode contacts and their respective stimulation amplitudes and polarities;
  perform an application of the patient specific electrical model to the distribution of the plurality of electrical stimuli;
  determine neural element activations of neural elements achieved based on the application of the patient specific electrical model to the distribution of the plurality of electrical stimuli;
  calculate a cost function result based on the electrical stimuli applied and the neural element activations achieved;
  perform a comparison of the cost function result to a cost function threshold;
  based on the comparison, adjust the inputs to the patient specific electrical model; and
  provide, to the spinal cord stimulation device, the optimized patient specific parameters.

* * * * *